United States Patent [19]

Böhm et al.

[11] 4,359,371
[45] Nov. 16, 1982

[54] PROCESS FOR PREPARING BROMINE- AND FLUORINE-CONTAINING HALOGENATED HYDROCARBONS

[75] Inventors: Horst Böhm; Werner Rudolph; Joachim Massonne, all of Hanover, Fed. Rep. of Germany

[73] Assignee: Kali-Chemie AG, Hanover, Fed. Rep. of Germany

[21] Appl. No.: 211,922

[22] Filed: Dec. 1, 1980

Related U.S. Application Data

[63] Continuation of Ser. No. 810,564, Jun. 27, 1977, abandoned.

[30] Foreign Application Priority Data

Jul. 2, 1976 [DE] Fed. Rep. of Germany ....... 2629775

[51] Int. Cl.$^3$ ............................................. C07C 17/20
[52] U.S. Cl. ................................ 204/163 R; 570/134; 570/137
[58] Field of Search ................................... 204/163 R

[56] References Cited

U.S. PATENT DOCUMENTS

| | | | |
|---|---|---|---|
| 2,639,301 | 5/1953 | Ruh et al. | 260/653 |
| 2,658,086 | 11/1953 | Ruh et al. | 260/653 |
| 3,377,393 | 4/1968 | Yale | 204/163 |
| 3,790,426 | 2/1974 | Schultz | 204/163 R |

FOREIGN PATENT DOCUMENTS 791702 8/1968 Canada .

*Primary Examiner*—Arthur P. Demers
*Attorney, Agent, or Firm*—Schwartz, Jeffery, Schwaab, Mack, Blumenthal & Koch

[57] ABSTRACT

A process for brominating fluorine-containing halogenated hydrocarbons is disclosed which comprises the step of reacting at least one halogenated fluorohydrocarbon compound of formula (I)

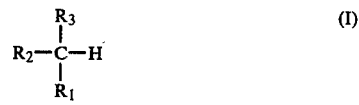

wherein
$R_1$ represents hydrogen, fluorine, chlorine, bromine or a lower alkyl group which is perhalogenated by a halogen selected from the group consisting of fluorine, chlorine and bromine;
$R_2$ represents hydrogen, fluorine, chlorine, or bromine, and;
$R_3$ represents fluorine or perfluorinated lower alkyl, in gaseous form with bromine under irradiation with light having a wavelength from about 250 nm to about 600 nm in the presence of an active amount of chlorine not exceeding about 2 moles per mole of bromine at a reaction temperature not exceeding 300° C., which is sufficient for transforming the reactants into sufficiently stable gaseous compounds and for substituting the hydrogen in a compound of formula (I) by bromine to form a compound of formula (II)

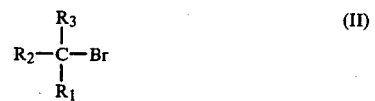

wherein $R_1$, $R_2$ and $R_3$ are as defined above.

10 Claims, No Drawings

PROCESS FOR PREPARING BROMINE- AND FLUORINE-CONTAINING HALOGENATED HYDROCARBONS

This is a continuation of application Ser. No. 810,564, filed June 27, 1977, now abandoned.

BACKGROUND OF THE INVENTION

The present invention relates to a process for brominating fluorine-containing halogenated hydrocarbons by reaction with bromine.

Contrary to unsubstituted hydrocarbons or chlorine-containing hydrocarbons, the bromination of which can be effected at temperatures less than 300° C., fluorinated hydrocarbons require a considerably higher temperature for bromination thereof. Thus, bromination of chloro-difluoromethane into bromo-chloro-difluoromethane by means of bromine is effected at 560° C. according to the process described in the German Auslegelschrift No. 1,168,404. The bromination of trifluoromethane into bromo-trifluoromethane according to the German Pat. No. 1,155,104 is effected at a temperature of between 650° and 800° C. The bromination of 1,1,1-trifluoro-2-chloroethane into 1,1,1-trifluoro-2-bromo-2-chloroethane according to the German Pat. No. 1,113,215 is effected at about 500° C.

An important disadvantage of these thermal bromination processes is the limited choice of reactor materials due to the necessarily high reaction temperatures. Thus, high temperature steels are not suitable and expensive special alloys having a high content in nickel are likewise only useful to a certain degree because of the highly corrosive behavior of elementary bromine and the hydrogen bromide formed within the reaction mixture. Materials based on silicates are also useless because of the presence of hydrogen fluoride within the reaction mixture.

A further disadvantage of the thermal bromination resides in the fact that, at the necessary high reaction temperatures, numerous side reactions take place like, e.g., chlorine-bromine exchange, splitting-off of hydrogen fluoride and cracking of the organic compounds under formation of numerous high boiling and, as well, tar- and coke-like products. These may cause considerable disturbances within the production process and may considerably lower the yield in desired raw products, whereby the economical value of the process is greatly decreased.

U.S. Pat. No. 2,658,086 discloses a process for brominating trifluoromethane into bromo-trifluoromethane by means of bromine in the presence of chlorine, yet without irradiation wherein the molar ratio between chlorine and bromine is not higher than 2. Yet this bromination occurs only at a temperature of about 450° C. and the yield is only 36.6 mole percent.

The bromination of trifluoromethane by means of bromine under irradiation with a mercury vapor lamp, but without addition of chlorine has been disclosed (see Corbett, Tarr and Whittle, Trans. Faraday Soc. 59 (1963), p. 1615). Yet, the described bromination can be observed only at temperatures of above 275° C.

SUMMARY OF THE INVENTION

It is an object of the present invention to provide a process for brominating fluorinated hydrocarbons by means of bromine which avoids the drawbacks attendant the state of the art, especially the formation of undesirable by-products.

It is a further object to provide such a process which can be effected at a relatively low temperature.

It is still a further object of the present invention to provide such a process which yields a high amount of the desired brominated reaction products.

It is yet a further object of the present invention to provide such a process which can be carried out in reactors of easily available, glass-like materials.

It is yet a further object of the present invention to provide such a process which is highly selective with regard to monobromination.

In order to accomplish the foregoing objects according to the present invention, there is provided a process for brominating fluorine-containing halogenated hydrocarbons which comprises the step of subjecting a mixture comprising at least one halogenated fluorohydrocarbon compound of formula (I)

wherein
$R_1$ represents hydrogen, fluorine, chlorine, bromine or a lower alkyl group which is perhalogenated by at least one halogen selected from the group consisting of fluorine, chlorine and bromine;
$R_2$ represents hydrogen, fluorine, chlorine, or bromine; and,
$R_3$ represents fluorine or perfluorinated lower alkyl, in gaseous form with bromine to irradiation with light having a wavelength from about 250 nm to about 600 nm in the presence of an active amount of chlorine not exceeding about 2 moles per mole of bromine at a reaction temperature not exceeding 300° C. which is sufficient for transforming the reactants into sufficiently stable gaseous compounds and for substituting the hydrogen in a compound of formula (I) by bromine to form a compound of formula (II)

wherein $R_1$, $R_2$ and $R_3$ are as defined above.

The process may be carried out in a continuous operation.

Further objects, features and advantages of the present invention will become apparent from the following detailed description of the invention and its preferred embodiments.

DETAILED DESCRIPTION OF PREFERRED EMBODIMENTS

In view of the above-mentioned prior art, it is surprising and could not be expected that the bromination of fluorinated hydrocarbons by means of bromine in the presence of chlorine and under irradiation according to the process of the present invention takes place already at temperatures of below 250° C. with a good reaction rate, a good yield per quantum of introduced light energy and with a high selectivity with regard to monobromination. Moreover, the reaction proceeds without any formation of tar- and coke-like by-products or any splitting-off of hydrogen fluoride.

Within the process of the present invention, all compounds of formula (I) can be reacted or all compounds of formula (II) can be obtained, respectively, which under the given reaction conditions, are transformable into a gaseous phase and are sufficiently stable. Preferably, these compounds contain 1 to 3 carbon atoms per molecule.

Such bromo- and bromo-chloro-fluorohydrocarbons which can be prepared according to the process of the present invention are valuable fire-extinguishing or cooling agents, e.g., brominated fluoromethane compounds, such as, bromo-chloro-difluoromethane ($CBrClF_2$) or bromo-trifluoromethane ($CBrF_3$) or inhalation-narcotics like, e.g., brominated fluoroethane compounds such as, 2-bromo-2-chloro-1,1,1-trifluoroethane ($CF_3CHBrCl$).

As will be further demonstrated in the examples below, according to the process of the present invention, a compound of formula (I) can be brominated at temperatures of from about 40° to about 250° C. The lower limit of this temperature range if in the range of the condensation point of the respective reaction mixture.

The molar ratio between chlorine and bromine should not exceed 2. Preferably, this ratio is between 1:1 to 1:4.

For example, trifluoromethane can be converted into bromo-trifluoromethane according to the equation

$$CHF_3 + \tfrac{1}{2}Br_2 + \tfrac{1}{2}Cl_2 \rightarrow CF_3Br + HCl$$

at a temperature of only 150° C. by irradiation with a high pressure mercury vapor lamp, whereby 17 mole percent of $CF_3Br$ are obtained from a starting mixture wherein the molar ratio of $CHF_3:Br_2:Cl_2$ is 2:1:0.5.

During the bromination of chloro-difluoromethane according to the present invention at a temperature of 90° C. under irradiation with a high pressure mercury vapor lamp, a reaction rate of 82 mole percent is achieved whereby from a starting mixture wherein the molar ratio of $CHClF_2:Br_2:Cl$ is 1:0.6:0.45, 75 mole percent of bromo-chloro-difluoromethane and 7 mole percent of dichloro-difluoromethane are formed relative to the starting $CHClF_2$.

No other by-products are formed in addition to the dichloro-difluoromethane. In this reaction, the quantum yield is more than 5 moles of bromo-chloro-difluoromethane per quantum mole of adsorbed irradiation energy.

The dichloro-difluoromethane which is formed as a by-product during the reaction by chlorination itself is a valuable cooling and aerosol expanding agent.

The process according to the present invention preferably is carried out in a continuous operation, wherein non-reacted starting material of formula (I), e.g., chloro-difluoromethane, bromine and optionally chlorine are recycled into the reactor after separation from the reacted mixture. The separation of gaseous reaction product may be effected, for example, in such a way that the major portion of the bromine is separated from the reaction gas in a stripping column, residual portions of bromine and chlorine subsequently are adsorbed by means of an appropriate adsorption agent and are recycled to the reactor by discontinuous desorption, subsequently the hydrogen chloride and residual parts of chlorine are adsorbed by water thereby forming hydrochloric acid. Remaining portions of chlorine and hydrogen chloride are removed by washing with sodium hydroxide solution and the remaining gaseous reaction mixture containing the organic components, such as, non-reacted starting material and reaction products, e.g., bromo-chloro-difluoromethane, chloro-difluoromethane and dichloro-difluoromethane, and optionally inert gases, is subsequently separated into its components by distillation under pressure.

Due to the fact that, during the reaction according to the present invention, no hydrogen fluoride is formed and the reaction temperatures are relatively low, glass-like materials, such as, e.g., boron silicate- or quartz glass can be used as reactor materials, especially for the irradiated portion of the reactor.

Even though the bromination of hydrocarbons in the presence of chlorine under the influence of actinic light is known in the art (see, German Pat. No. 767,822, Italian Pat. No. 688,549; Recl. Trav. Chem. Pays-Bas 92 (1973) pp. 161–173) it could not be expected that in spite of the well known lack of reactivity of the hydrogen bond in fluorinated and chlorinated hydrocarbons which is caused by the fluorine substituents in the molecule, such hydrogen could be substituted by bromine already at temperatures of below 250° C. at a high reaction speed in a selective reaction with a good quantum yield.

During the process according to the present invention, before or during the reaction, bromo-chloride is formed from the introduced bromine and chlorine corresponding to the respective thermodynamic equilibrium conditions. For this reason, instead of bromine and chlorine, bromo-chloride may also be used, optionally in admixture with a stoichiometrically excessive amount of bromine or chlorine.

As can be seen from the examples below, in addition to the reaction temperature, the adsorbed irradiation and the flow conditions for the gaseous reaction mixture, the molar ratio between bromine and chlorine likewise influences the speed and the selectivity of the photochemical brominating reaction according to the process of the present invention.

Although the maximum adsorption of irradiation energy in the gaseous phase is at 330 nm for chlorine, at 375 nm for bromo-chloride and at 415 nm for bromine (J. Phys. Chem. 68 (1964) p. 2264), the selectivity of the reaction is hardly influenced if considerably portions within the wavelength range of the adsorbed irradiation are between 250 nm and 350 nm.

Due to the irradiation adsorbing behavior of bromo-chloride, the reaction can also be effected in a wavelength range of below 250 nm, if the irradiation adsorbing behavior of the respective organic compounds allows for this.

Suitable irradiation sources for the process according to the present invention are, for example, commercially available metal vapor- and noble gas discharge tubes exhibiting a good energy yield and a sufficient intensity of the emitted irradiation in the wavelength range of from 250 nm to 450 nm, such as, high pressure mercury vapor- or xenon lamps. Either one or several irradiation sources may be used. In addition to the ring slot reactor provided with an axial irradiation source which is used within the examples below, differently constructed photoreactors which are suitable for fluid phases can also be used, for example, reactors as are disclosed in Kirk-Othmer, Encyclopedia of Chemical Technology, 2nd Ed., Vol. 15 (1968) pp. 346–354, the disclosure of which is hereby incorporated by reference and in Ullmanns Encyklopaedie der Technischen Chemie, 4th Ed., Vol. 3 (1973), pp. 311-314, the disclosure of which is also hereby incorporated by reference.

The present invention will now be described with reference to the following examples, which are intended to be illustrative only.

TEST ARRANGEMENT FOR EXAMPLES 1-8

Measured amounts of the hydrogen-containing fluoro- or chloro-fluorohydrocarbons are mixed with bromine and chlorine and introduced into the reaction vessel in gaseous form. This reaction vessel is a ring slot reactor made of boron silicate glass provided with an outer tempering jacket. The high pressure mercury vapor lamp (type, TQ500, manufacturer, Original Hanau Quarzlampen GmbH., output—500 watts, wavelength range—200-600 nm) is situated in the central inner tube of the reactor.

The length of the reaction ring slot is 400 mm and the volume of the irradiated reaction space is 436 ml at a ring slot breadth of 14 mm. Alternatively, a reactor having the same structural parameters but made from quartz glass is used. Silicone oil is used as the tempering means. The reaction mixture is introduced into the irradiation zone at the lower part of the reactor at the temperature of the silicone oil. It leaves the reactor at the upper end to subsequently be washed to neutral in a gas washing operation by means of sodium hydroxide solution. The composition of each of the gaseous reaction products is determined by gas chromatography. The temperatures that are given in the examples are the temperatures which are measured in the silicone oil.

EXAMPLE 1

In a testing apparatus mode from boron silicate glass, chloro-difluoromethane is reacted with bromine at 168° C., thereby maintaining a constant molar ratio $CHF_2Cl:Br_2:Cl_2$ of 1:0.74:0.35. The following Table shows the composition of the organic components of the gaseous reaction product at different discharge rates.

| $CHF_2Cl$ mole/h | Composition of the gaseous reaction product (mole %) | | | | Yield in $CF_2ClBr$ relative to the reacted amount of $CHF_2Cl$ (%) |
| --- | --- | --- | --- | --- | --- |
| | $CHF_2Cl$ | $CF_2Cl_2$ | $CF_2ClBr$ | remainder | |
| 4 | 36.3 | 5.2 | 58.4 | 0.1 | 91 |
| 8 | 45.2 | 5.1 | 49.6 | <0.1 | 90 |
| 12 | 51.7 | 5.0 | 43.3 | — | 89 |

The contact times are 5.2 sec., 3.4 sec. and 1.7 sec., respectively.

EXAMPLE 2

In a testing apparatus made from boron silicate glass, chloro-difluoromethane is reacted with bromine thereby maintaining a constant discharge rate of $CHF_2Cl$ and a constant molar ratio of $CHF_2Cl:Br_2$. During this experiment, the amounts of chlorine which are introduced are varied. The $CHF_2Cl$— discharge rate is 4 moles/hour, the reaction temperature is 172° C.

| Molar ratio $CHF_2Cl:Br_2:Cl_2$ | Compositon of the gaseous reaction product (mole %) | | | | Yield in $CF_2ClBr$ relative to the reacted amount of $CHF_2Cl$ (%) |
| --- | --- | --- | --- | --- | --- |
| | $CHF_2Cl$ | $CF_2Cl_2$ | $CF_2ClBr$ | remainder | |
| 1:0.57:0.15 | 70.0 | 0.6 | 29.4 | — | 98 |
| 1:0.57:0.32 | 40.3 | 3.8 | 55.8 | <0.1 | 94 |
| 1:0.57:0.40 | 26.5 | 5.9 | 67.5 | 0.1 | 91 |
| 1:0.57:0.60 | 12.0 | 18.4 | 69.5 | 0.1 | 78 |
| 1:0.57:1.23 | 0.3 | 47.9 | 51.8 | — | 51 |

The contact times range from 3.8 to 6.2 seconds.

EXAMPLE 3

In this example, varying amounts of bromine are added, and a constant $CHF_2Cl$— discharge rate of 4 moles/hour and a constant introduction of chlorine of 1.2 moles/hour are maintained. The results from this experiment are shown in the following Table. A boron silicate glass reactor is used. The reaction temperature is 169° C.

| Molar ratio $CHF_2Cl:Br_2:Cl_2$ | Composition of the gaseous reaction product (mole %) | | | | Yield in $CF_2ClBr$ relative to the reacted amount of $CHF_2Cl$ (mole %) |
| --- | --- | --- | --- | --- | --- |
| | $CHF_2Cl$ | $CFCl_2$ | $CF_2ClBr$ | remainder | |
| 1:0.25:0.30 | 45.5 | 5.5 | 49.0 | — | 90 |
| 1:0.52:0.30 | 44.5 | 2.3 | 53.2 | — | 95 |
| 1:0.73:0.30 | 48.2 | 2.2 | 49.6 | — | 95 |
| 1:0.99:0.30 | 56.4 | 1.3 | 42.2 | 0.1 | 96 |

The contact times range from 4.7 to 7.0 seconds.

EXAMPLE 4

In a photo-bromination reactor made of boron silicate glass, 4 moles/hours of $CHF_2Cl$, 3 moles/hour of bromine and 1 mole/hour of chlorine are continuously introduced and reacted. During the experiment, the temperature is varied within a range of from 60° to 200° C. The test results are given in the Table below.

| Reactor temperature (°C.) | Composition of the gaseous reaction product (mole %) | | | | Yield in $CF_2ClBr$ relative to the reacted amount of $CHF_2Cl$ (mole %) |
| --- | --- | --- | --- | --- | --- |
| | $CHF_2Cl$ | $CF_2Cl_2$ | $CF_2ClBr$ | remainder | |
| 85 | 61.3 | — | 38.6 | <0.1 | 99 |
| 100 | 55.7 | 0.1 | 44.2 | — | 99 |
| 154 | 36.0 | 4.9 | 59.0 | 0.1 | 92 |
| 200 | 26.7 | 5.9 | 67.3 | 0.1 | 91 |

The contact times range from 5.0 to 6.7 seconds.

EXAMPLE 5

In a testing apparatus made of quartz glass, 6 moles/hour of $CHF_2Cl$ are reacted with 4.5 moles/hour of bromine and 2.1 moles/hour of chlorine at a temperature of 172° C. The composition of the organic components of the reaction product as determined by gas chromatography is as follows:

$CHF_2Cl$: 20.4 mole percent
$CF_2ClBr$: 74.5 mole percent
$CF_2Cl_2$: 5.1 mole percent
The contact time is 3.4 seconds.

EXAMPLE 6

4.0 moles/hour of $CHF_3$ and 2 moles/hour of bromine together with 1.0 moles/hour of chlorine are introduced into the quartz glass irradiation reactor and are irradiated at a temperature of 150° C.

After being washed to neutral, the gaseous reaction mixture has the following composition:

$CHF_3$: 81.5 mole percent
$CF_3Br$: 16.8 mole percent
$CF_3Cl$: 1.6 mole percent
The contact time is 6.4 seconds.

EXAMPLE 7

Into the boron silicate glass test apparatus, 2 moles/hour of 1,2-dichloro-1,2,2-trifluoroethane, 1.4 moles/hour of bromine and 0.6 moles/hour of chlorine are introduced and are irradiated at a temperature of 148° C.

The resulting gaseous mixture has the following composition:

$CHFCl-CF_2Cl$: 56.3 mole percent
$CFClBr-CF_2Cl$: 35.5 mole percent
$CFCl_2-CF_2Cl$: 7.4 mole percent
By-products: 0.8 mole percent The yield in 1-bromo-1,2-dichloro-1,2,2-trifluoroethane is 81 mole percent relative to the reacted amount of starting material.

EXAMPLE 8

4 moles/hour of 2-chloro-1,1,1-trifluoroethane and 1 mole/hour of bromine, together with 0.6 moles/hour of chlorine are introduced into the boron silicate glass test apparatus at a temperature of 110° C. The composition of the organic components of the resulting gaseous reaction mixture is as follows:

$CF_3-CH_2Cl$: 88.3 mole percent
$CF_3-CHCl_2$: 0.9 mole percent
$CF_3-CCl_3$: <0.1 mole percent
$CF_3-CHClBr$: 10.3 mole percent
$CF_3-CClBr_2$: 0.4 mole percent

EXAMPLE 9

In the following experiment, the same test arrangement as described above is used, except a high pressure mercury vapor lamp having an output of 2 kW is used. Corresponding to the dimensions of the mercury vapor lamp, a boron silicate glass ring slot reactor provided with an outer tempering jacket is used, the reactor volume of which is 5,710 ml, the reactor length being 1,180 mm. The high pressure mercury vapor lamp in the central inner space is a lamp of the type TQ 2024 50 Zl, and provides an additional irradiation intensity in the range of 400 nm to 450 nm. The manufacturer of this lamp is the company Original Hanau Quarzlampen GmbH., Hanua. The reactor temperature is adjusted to 90° C. by means of a thermostat. A gas mixture consisting of 16.7 moles/hour of $CHF_2Cl$, 10.0 moles/hour of bromine and 7.5 moles/hour of chlorine is introduced into the reactor for the photo-reaction. After a neutralizing washing, wherein all acidic components are removed, the composition of the remaining gaseous reaction mixture is determined by gas chromatography. The results are as follows:

$CHF_2Cl$: 17.1 mole percent
$CF_2Cl_2$: 7.4 mole percent
$CF_2ClBr$: 75.4 mole percent The yield in bromo-chloro-difluoromethane is 91% relative to the amount of reacted chloro-difluoromethane. The quantum yield is more than 5 moles of $CF_2ClBr$ per quantum mole of adsorbed irradiation. The contact time is 1.5 seconds.

While the invention has now been described in terms of various preferred embodiments, and exemplified with respect thereto, the skilled artisan will readily appreciate that various substitutions, changes, modifications, and omissions may be made without departing from the spirit thereof. Accordingly, it is intended that the scope of the invention be limited solely by that of the following claims.

What is claimed is:

1. A process for brominating fluorine-containing halogenated hydrocarbons which comprises the step of subjecting a vapor phase mixture comprising at least one halogenated fluorohydrocarbon compound selected from $CHF_2Cl$ and $CHF_3$ and bromine to irradiation with light having a wavelength of from about 250 nm to about 600 nm in the presence of an active amount of chlorine, not exceeding about 2 moles per mole of bromine at a reaction temperature below 200° C. which is sufficient for substituting the hydrogen in said halogenated fluorocarbon compound by bromine and at a contact time of between about 1.5 and 7 seconds.

2. A process as defined in claim 1, wherein the molar ratio between chlorine and bromine is between about 1:1 and about 1:4.

3. A process as defined in claim 2, wherein said molar ratio is between about 1:1 and about 1:2.

4. A process as defined in claim 1, wherein the wavelength is from about 250 nm to about 450 nm.

5. A process as defined in claim 1, wherein the reaction temperature is less than 150° C.

6. The process as defined in claim 2, wherein bromo-chloro-difluoromethane is obtained from chlorodifluoromethane at a temperature between about 85° C. and 172° C.

7. A process as defined in claim 6, wherein the temperature is about 172° C.

8. A process as defined in claim 6, wherein the temperature is about 154° C.

9. A process as defined in claim 6, wherein the temperature is about 100° C.

10. A process as defined in claim 2, wherein bromotrifluoromethane is obtained from trifluoromethane at a temperature of about 150° C.

* * * * *